United States Patent [19]

Tolbert et al.

[11] 4,253,684
[45] Mar. 3, 1981

[54] QUICK CONNECT COUPLER WITH AIR SHIELD

[75] Inventors: William R. Tolbert, Manchester; Joseph Feder, University City, both of Mo.

[73] Assignee: Monsanto Company, St. Louis, Mo.

[21] Appl. No.: 39,086

[22] Filed: May 14, 1979

[51] Int. Cl.³ .............................................. F16L 55/00
[52] U.S. Cl. ..................................... 285/13; 128/247; 34/242; 285/133 R; 285/156; 285/174; 285/304; 285/404
[58] Field of Search ....................... 285/13, 14, 10, 11, 285/305, 133 R, 138, 156, 304, 404, 3, 137 R, 316, 317, 277, DIG. 22, 347, DIG. 15, 174; 128/1 R, 1 B, 247; 137/241; 34/242, 107; 277/DIG. 1, 135

[56] References Cited

U.S. PATENT DOCUMENTS

| 3,170,667 | 2/1965 | Szohatzky | 285/DIG. 15 |
|---|---|---|---|
| 3,385,036 | 5/1968 | Webb | 128/1 B |
| 3,394,954 | 7/1968 | Sarns | 285/347 X |
| 3,761,117 | 9/1973 | Shendure | 285/277 X |
| 3,955,833 | 5/1976 | Silbert | 285/3 X |
| 4,019,512 | 4/1977 | Tenczar | 285/3 X |
| 4,022,205 | 5/1977 | Tenczar | 285/3 X |
| 4,030,494 | 6/1977 | Tenczar | 285/3 X |
| 4,114,853 | 9/1978 | Medvick | 285/316 X |
| 4,116,476 | 9/1978 | Porta et al. | 285/317 |
| 4,123,091 | 10/1978 | Cosentino et al. | 285/DIG. 22 |
| 4,150,494 | 4/1979 | Rothchild | 34/242 |

FOREIGN PATENT DOCUMENTS 855040  11/1960  United Kingdom ..................... 277/135

Primary Examiner—Dave W. Arola
Attorney, Agent, or Firm—Scott J. Meyer; James W. Williams, Jr.

[57] ABSTRACT

A quick connect coupler for fluid transfer is disclosed in which one or both of the mating coupler members is provided with a sleeve which encloses at least a portion of said coupler member adjacent to its coupling end. The sleeve has an inlet for admission of air through its outer wall, a narrow concentric gap between its inner wall and the enclosed coupler member at said coupling end, and a passageway leading from said air inlet to said concentric gap for passage of air over said coupling end. The coupler is adapted for repeated connecting and disconnecting by cooperating releasable coupling means without loss of sterility by virtue of an air shield which is produced over said coupling end by passage of sterile air through the concentric gap.

4 Claims, 6 Drawing Figures

QUICK CONNECT COUPLER WITH AIR SHIELD

BACKGROUND OF THE INVENTION

This invention relates to the field of sterile fluid connectors or couplers such as may be used, for example, in the transfer of fluids used in cell culture systems, in the collection and delivery of blood and blood components, in the handling of kidney dialysis fluids and in the administration of parenteral solutions.

In many such cases it is desirable that the tubing or conduits used in the apparatus for dispensing and transfer of fluids be provided with a quick connect or quick change coupler so that the tubing can be rapidly connected and disconnected, especially in emergency or life-saving situations. Maintenance of sterility and the prevention of microbial contamination is a critical consideration in the use of such couplers.

Numerous such quick connect couplers have been developed heretofore. The Sarns coupler described in U.S. Pat. No. 3,394,954 and the Swagelok coupler disclosed in U.S. Pat. No. 4,114,853 are typical examples of commercially successful quick connect couplers. Most of these coupler devices are adapted to being sterilized by autoclaving or steam sterilizing, or washing with sterilizing solutions or by exposure to sterilizing gases.

Other fluid couplers as illustrated, for example, in U.S. Pat. Nos. 3,955,833, 4,019,512 and 4,022,205, have internal protective membranes of one sort or another which act as barriers against contamination of the coupling unit before and during use. These couplers generally are of the disposable plastic type adapted for a single use. After opening of the connection the sterility is lost and the device must be either discarded after a single use or resterilized before repeat use.

A quick connect coupler which can be subjected to repeated and convenient connecting and disconnecting without loss of sterility and without the need for resterilizing after each use would be of considerable practical value.

BRIEF DESCRIPTION OF THE INVENTION

In accordance with the present invention, a fluid coupler of the quick connect type is provided which can be subjected to repeated connecting and disconnecting without loss of sterility. This coupler comprises first and second coupler members, each said coupler member having a body, a fluid passageway through said body and adapted to be joined to a fluid source at one end and having an opposite end adapted for mutual coupling with the other coupler member by cooperating releasable coupling means. A sleeve encloses the body of at least one of said coupler members over at least a portion of the length of said body adjacent to its coupling end. The sleeve has an air inlet for admission of sterile air through its outer wall, a narrow concentric gap or annulus between the inner wall of said sleeve and the outer wall of the enclosed coupler member at said coupling end, and an air passageway leading from said air inlet to said concentric gap for passage of air over the coupling end of said enclosed coupler member. By passage of sterile air through the sleeve and out the concentric gap, the coupler member at its coupling end is protected from airborne contaminants that would otherwise cause loss of sterility.

DETAILED DESCRIPTION OF THE INVENTION

While the specification concludes with claims particularly pointing out and distinctly claiming the subject matter regarded as forming the present invention, it is believed that the invention will be better understood from the following exemplary description taken in connection with the accompanying drawings in which:

Figure 1:
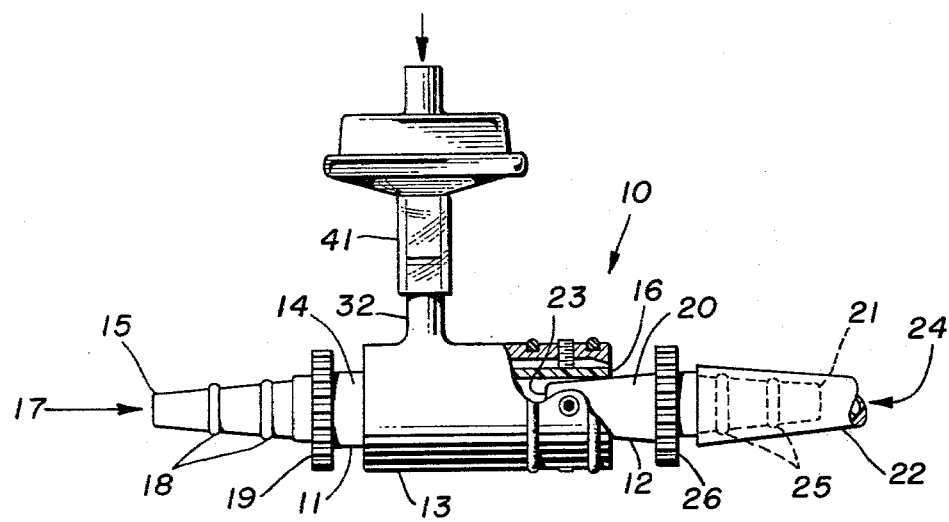
FIG. 1 is a side elevational view partially in cross section showing coupling engagement of coupler members with an air shield sleeve element positioned over one of said coupler members.

Turning now to the figures, reference numeral 10 refers generally to an air shielded quick connect coupler. The coupler 10 comprises interconnectable first and second axially aligned coupler members 11 and 12 and an air shield sleeve element 13 disposed over a portion of coupler member 11. Coupler member 11 has a generally tubular body 14, and end 15 adapted for joining to a fluid conduit (not shown), an opposite coupling end 16 for interconnecting with coupler member 12, and an axial bore 17 for passage of fluid therethrough. Coupler member 12 also has a generally tubular body 20, an end 21 adapted for joining to a fluid conduit 22 (shown in part), an opposite coupling end 23 for interconnecting with coupler member 11, and an axial bore 24 for passage of fluid therethrough. Coupler member 11 and 12 are shown to be provided on their outer walls with annular ridges 18 and 25, respectively, for gripping fluid conduits such as, for example, plastic or rubber tubing which can be forced over ends 15 and 21, respectively, to provide fluid tight seals. Circumferentially disposed knurled finger grips 19 and 26 are adapted for manual coupling of coupler members 11 and 12. In this embodiment, coupler members 11 and 12 preferably are fabricated of a rigid plastic material such as, for example, linear polyethylene. The slightly tapered coupling end 23 of the stem coupler member 12 can be gently forced into the opening of body coupler member 11 with a twisting motion to provide a snug friction coupling.

Figure 2:
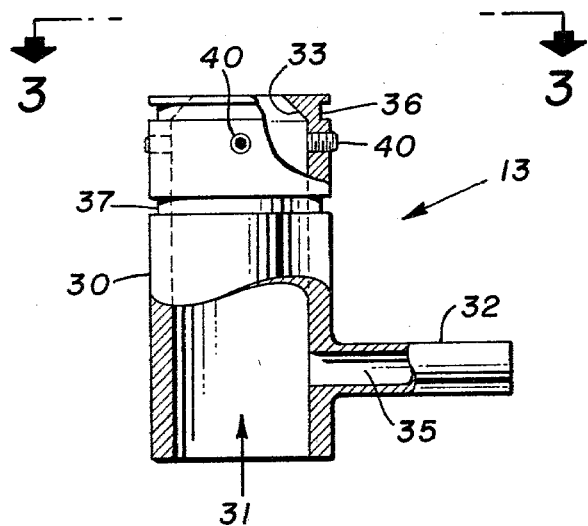
FIG. 2 is a side elevational view of the air shield sleeve element of FIG. 1 on a larger scale, in greater detail, and rotated in a vertical orientation.
Figure 3:
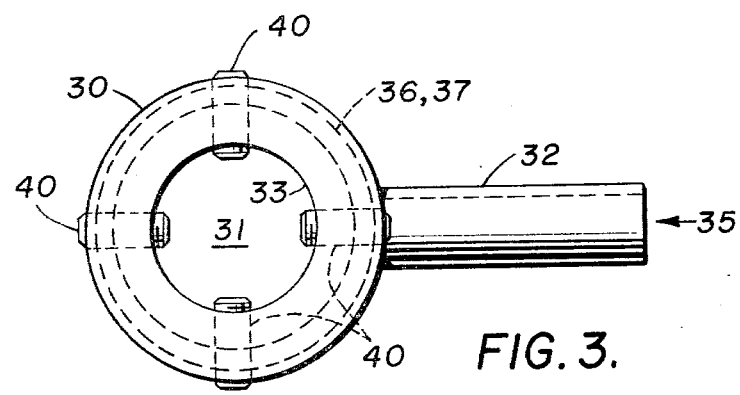
FIG. 3 is an end view of the air shield sleeve element of FIG. 2.
Figure 4:
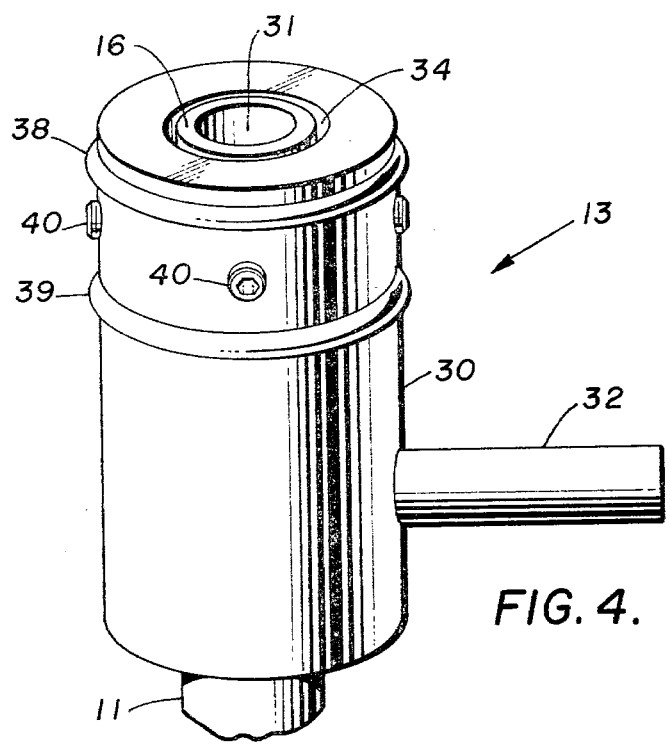
FIG. 4 is a perspective view of the air shield sleeve element of FIG. 2 showing the coupling end of an enclosed coupler member.
Figure 5:
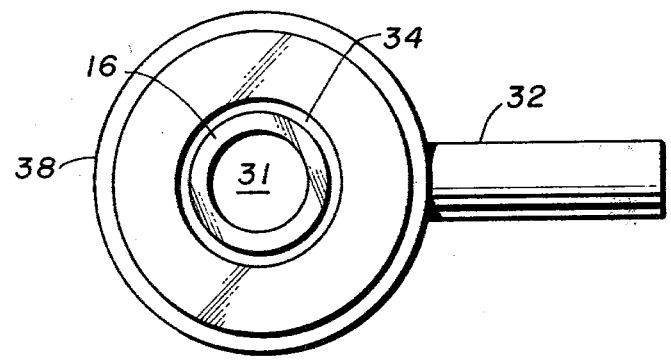
FIG. 5 is an end view of the air shield sleeve element of FIG. 4.

FIGS. 2 and 3 show the air shield sleeve element 13 of FIG. 1 in greater detail. It will be seen that sleeve 13 has a generally cylindrical body 30, an axial bore 31 and an air inlet arm 32 projecting from one side of the body. Sleeve 13 is adapted for closely fitting over either of the coupler members 11 and 12. A beveled edge 33 is provided in the inner wall at the distal end of the sleeve to provide a relatively constricted opening. In FIGS. 4 and 5 it will be seen that the beveled edge of the sleeve provides for a narrow concentric gap or annulus 34 between the inner wall of the sleeve and the outer wall of the coupler member at its coupling end 16. Arm 32 is essentially a tubular member with a bore 35 which opens at one end into the inner portion of sleeve 13 and is adapted for attachment to an air line at the opposite end. When placed over the coupler member, sleeve 13 provides a passageway for air entering arm 32 which will spread over the body of the coupler member and be exhausted through concentric gap 34. The opposite end of the sleeve is sealed over the coupler member to prevent escape of air at said opposite end.

As shown in FIGS. 2 and 3, air shield sleeve element 13 is provided with a pair of outer concentric grooves 36 and 37 which are adapted for placement therein of O-ring seals 38 and 39 as seen in FIGS. 4 and 5. A protective cup-like cover (not shown) can thereby be readily placed over the open end of the air shield sleeve element and can be sealingly closed to protect said sleeve and the enclosed coupling end 16 from airborne contaminants after the coupler member is disconnected from the mating coupler member and when not in use. A conventional air filter 41 as shown in FIG. 1 can be attached to arm 32 to maintain sterility of air which is pumped into the air shield sleeve element during use of the quick connect coupler.

The air shield sleeve element can be used for placement over a body or female coupler member as shown, or over a stem or male coupler member, or similar sleeve elements can be placed over each coupler member. A series of set screws 40 can be used to tighten the air shield over the body of the coupler member.

A most important feature found in the fluid quick connect coupler of the present invention is the narrow concentric gap or annulus between the internal edge of the air shield sleeve element and the outer wall of the coupler member at its coupling end. This gap preferably is from about 0.001 to about 0.025 inches and most preferably about 0.007 inches. Sterile air can be forced through this gap preferably at a flow rate of from about 2 to about 10 liters per minute. With use of a beveled edge on the sleeve element of from about 30° to about 60° and preferably about 45° as shown in FIG. 2, the air forms a cone which intersects between about 0.5 and about 2 cm. from the coupling end. This cone of sterile air protects the coupler from airborne contaminants during connecting and disconnecting of the two coupler members for liquid transfer therebetween.

Figure 6:
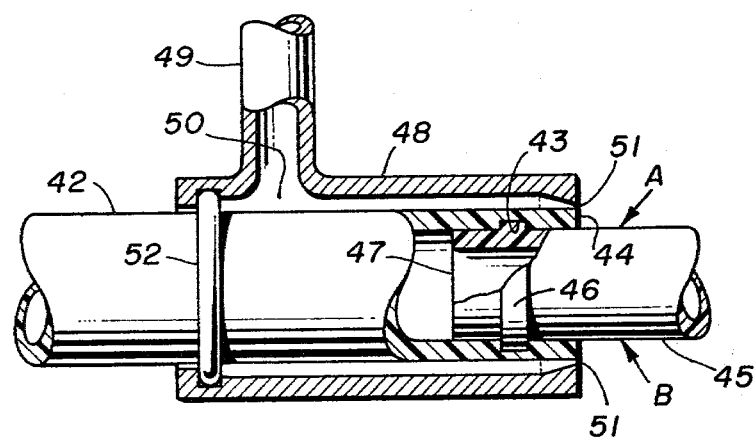
FIG. 6 is a sectional view similar to that of FIG. 1 but with portions removed and depicting the coupling engagement and air shield aspects of another embodiment in greater detail.

It will be appreciated that the invention is not limited to any particular structural configuration of the two coupler members so long as they are adapted for quick connect coupling by cooperating releasable coupling means at one end and for joining to a fluid source such as a fluid conduit or fluid receptacle at the opposite end. Thus, FIG. 6 illustrates another embodiment of the cooperating releasable coupling means. As shown in part, body coupler member 42 is provided with a detent or groove 43 at its coupling end 44 while stem coupler member 45 is provided with an annular projection or ridge 46 at its coupling end 47. In this embodiment, coupler members 42 and 45 preferably are fabricated of a resilient flexible plastic material. The frictional engagement of projection 46 with detent 43 can be overcome by the simple expedient of applying pressure at points A and B in conjunction with a push-in connection or pull disconnect. Air shield sleeve element 48 is seen to be disposed in a relatively closely fitting relationship over coupler member 42 at the coupling end of said coupler member. Air can enter air inlet arm 49, traverse passageway 50 and exit through the narrow concentric gap 51 between the inner wall of said sleeve and the outer wall of the enclosed coupler member. An O-ring seal 52 disposed over the body of coupler member 42 provides an air tight seal with the air shield sleeve element. Instead of the annular projection and detent coupling as shown in FIG. 6, body coupler member 42 can be provided with a latch projection at its coupling end which is adapted to snap over a shoulder at the coupling end of stem member 45.

The present invention also is particularly well adapted for use of the air shield sleeve element over quick connect couplers of the types described in U.S. Pat. Nos. 3,170,667, 3,761,117, and 4,114,853. These are ball lock type quick connect couplers having a spring biased sleeve element mounted about a body coupler member and a stem coupler member adapted to be telescoped into the body coupler member. The spring biased sleeve element is adapted to retain ball elements in place in the body coupler member in either a locked or unlocked position with respect to a circumferential groove in the stem coupler member. These ball members serve the same function as projection 46 in the embodiment of FIG. 6 while the groove functions as detent 43.

The air shielded quick connect coupler of this invention is especially desirable for use with large vessels which are placed in a relatively fixed or stationary position and therefore not readily adapted for carrying into a laminar flow hood during fluid transfer operations. For example, large scale cell culture reactor and storage vessels may require systems for aseptic addition and removal of various solutions. While movable fluid conduits having the stem member of the quick connect coupler may conveniently be carried into a laminar flow hood, the body member of the quick connect coupler which may be attached directly to the cell culture vessel could not similarly be conveniently carried into the laminar flow hood. Also, in some cases it is readily simple to autoclave or flame one coupler member of the quick connect coupler but not the other coupler member due to their relative locations in the apparatus. In other cases, where it is inconvenient to autoclave or flame either coupler member, it is preferable to provide both coupler members with the air shield sleeve elements.

Various other modifications and adaptations of the invention will be apparent to the person skilled in the art after reading the present disclosure without departing from the spirit and scope of the invention and it is intended that all such modifications and adaptations come within the scope of the appended claims.

What is claimed is:

1. An air shielded quick connect coupler comprising first and second coupler members, each said coupler member having a body, a fluid passageway through said body and adapted to be joined to a fluid source at one end and having an opposite end with cooperating releasable coupling means adapted for mutual coupling with the other coupler member, a sleeve which encloses the body of at least one of said coupler members over at least a portion of the length of said body adjacent to its coupling end, said sleeve being open at its distal end around the coupling end of said coupler member and being closed at its opposite end over said coupler member, and said sleeve having an air inlet for admission of air through its outer wall, a narrow concentric gap between the inner wall of said sleeve and the outer wall of said enclosed coupler member at said coupling end, and an air passageway leading from said air inlet to said concentric gap for passage of air through said sleeve and exiting at the distal end of said sleeve over the coupling end of said enclosed coupler member.

2. The air shielded quick connect coupler of claim 1 in which the coupler members are body and stem members having friction coupling means.

3. The air shielded quick connect coupler of claim 1 in which the coupler members are body and stem members having cooperating annular projection and detent coupling means.

4. The air shielded quick connect coupler of claim 1 in which said sleeve has a beveled inner edge at its distal end which restricts the concentric gap between the inner wall of said sleeve and the outer wall of said enclosed coupler member, such that air passing through said concentric gap will tend to form in an intersecting conical pattern.

* * * * *